US00PP22887P2

(12) United States Plant Patent
Bernuetz

(10) Patent No.: US PP22,887 P2
(45) Date of Patent: Jul. 24, 2012

(54) ***BRACHYSCOME* PLANT NAMED 'BONBRA7115'**

(50) Latin Name: *Brachyscome×hybrida*
Varietal Denomination: Bonbra7115

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 11 days.

(21) Appl. No.: 12/930,053

(22) Filed: Dec. 24, 2010

(51) Int. Cl.
*A01H 5/00* (2006.01)

(52) U.S. Cl. ..... Plt./411

(58) Field of Classification Search ..... Plt./411
See application file for complete search history.

*Primary Examiner* — Susan McCormick Ewoldt
(74) *Attorney, Agent, or Firm* — C. A. Whealy

(57) ABSTRACT

A new and distinct cultivar of *Brachyscome* plant named 'Bonbra7115', characterized by its compact and upright plant habit; freely branching growth habit, bushy growth form; numerous inflorescences positioned above the foliar plane; bright yellow-colored ray florets; and good postproduction longevity and garden performance.

1 Drawing Sheet

Botanical designation: *Brachyscome×hybrida*.
Cultivar denomination: 'BONBRA7115'.

BACKGROUND OF THE INVENTION

The present invention relates to a new and distinct cultivar of *Brachyscome* plant, botanically known as *Brachyscome× hybrida* and hereinafter referred to by the name 'Bonbra7115'.

The new *Brachyscome* plant is a product of a controlled breeding program conducted by the Inventor in Yellow Rock, New South Wales, Australia. The objective of the breeding program is to create new mounding *Brachyscome* plants with unique and attractive ray floret color.

The new *Brachyscome* plant originated from a cross-pollination in August, 2004 in Yellow Rock, New South Wales, Australia, of a proprietary selection of *Brachyscome×hybrida* identified as code number 00-127.1, not patented, as the female, or seed, parent with a proprietary selection of *Brachyscome×hybrida* identified as code number 00-147.6, not patented, as the male, or pollen, parent. The new *Brachyscome* plant was discovered and selected by the Inventor as a single flowering plant from within the progeny of the stated cross-pollination in a controlled environment in Yellow Rock, New South Wales, Australia in April, 2005.

Asexual reproduction of the new *Brachyscome* plant by vegetative cuttings in a controlled environment in Yellow Rock, New South Wales, Australia since May, 2005, has shown that the unique features of this new *Brachyscome* plant are stable and reproduced true to type in successive generations.

SUMMARY OF THE INVENTION

Plants of the new *Brachyscome* have not been observed under all possible environmental conditions. The phenotype may vary somewhat with variations in environmental conditions such as temperature and light intensity without, however, any variance in genotype.

The following traits have been repeatedly observed and are determined to be the unique characteristics of 'Bonbra7115'.

These characteristics in combination distinguish 'Bonbra7115' as a new and distinct *Brachyscome* plant:

1. Compact and upright plant habit.
2. Freely branching growth habit, bushy growth form.
3. Numerous inflorescences positioned above the foliar plane.
4. Bright yellow-colored ray florets.
5. Good postproduction longevity and garden performance.

Plants of the new *Brachyscome* differ primarily from plants of the female parent selection in the following characteristics:

1. Plants of the new *Brachyscome* have smaller inflorescences than plants of the female parent selection.
2. Plants of the new *Brachyscome* and the female parent selection differ in ray floret color as plants of the female parent selection have pink-colored ray florets.

Plants of the new *Brachyscome* differ primarily from plants of the male parent selection in the following characteristics:

1. Plants of the new *Brachyscome* are more compact and bushier than plants of the male parent selection.
2. Plants of the new *Brachyscome* have smaller leaves than plants of the male parent selection.

Plants of the new *Brachyscome* can also be compared to plants of the *Brachyscome angustifolia* 'Billabong Mauve Delight', disclosed in U.S. Plant Pat. No. 10,889. In side-by-side comparisons conducted in Yellow Rock, New South Wales, Australia, plants of the new *Brachyscome* differed primarily from plants of 'Billabong Mauve Delight' in the following characteristics:

1. Plants of the new *Brachyscome* were narrower than plants of 'Billabong Mauve Delight'.
2. Plants of the new *Brachyscome* had slightly smaller inflorescences than plants of 'Billabong Mauve Delight'.
3. Plants of the new *Brachyscome* had more ray florets per inflorescence than plants of 'Billabong Mauve Delight'.
4. Plants of the new *Brachyscome* and 'Billabong Mauve Delight' differed in ray floret color as plants of 'Billabong Mauve Delight' had light purple-colored ray florets.

BRIEF DESCRIPTION OF THE PHOTOGRAPHS

The accompanying colored photographs illustrate the overall appearance of the new *Brachyscome* plant showing the colors as true as it is reasonably possible to obtain in colored reproductions of this type. Colors in the photographs may differ slightly from the color values cited in the detailed botanical description which accurately describe the colors of the new *Brachyscome* plant.

The photograph at the top of the sheet comprises a side perspective view of a typical flowering plant of 'Bonbra7115' grown in a container.

The photograph at the bottom of the sheet is a close-up view of typical inflorescences of 'Bonbra7115'.

DETAILED BOTANICAL DESCRIPTION

The aforementioned photographs and following observations, measurements and values describe plants grown during the summer in 15-cm containers in an outdoor nursery in Higashiomi, Shiga, Japan and under commercial practices. During the production of the plants, day temperatures averaged 28° C. and night temperatures averaged 20° C. Plants were five and four months old when the photographs and description, respectively, were taken. In the following description, color references are made to The Royal Horticultural Society Colour Chart, 2007 Edition, except where general terms of ordinary dictionary significance are used.

Botanical classification: *Brachyscome×hybrida* 'Bonbra7115'.

Parentage:

*Female, or seed, parent*.—Proprietary selection of *Brachyscome×hybrida* identified as code number 00-127.1, not patented.

*Male, or pollen, parent*.—Proprietary selection of *Brachyscome×hybrida* identified as code number 00-147.6, not patented.

Propagation:

*Type*.—By vegetative cuttings.

*Time to initiate roots, summer*.—About seven days at temperatures of 20° C. to 25° C.

*Time to initiate roots, winter*.—About ten days at temperatures of 15° C. to 20° C.

*Time to produce a rooted young plant, summer*.—About three weeks at temperatures of 20° C. to 25° C.

*Time to produce a rooted young plant, winter*.—About four weeks at temperatures of 15° C. to 20° C.

*Root description*.—Fibrous; white in color.

*Rooting habit*.—Freely branching; medium density.

Plant description:

*Plant form and growth habit*.—Compact and upright plant habit; moderately vigorous growth habit; freely branching growth habit and bushy plant form; pinching enhances lateral branch development.

*Plant height*.—About 20.2 cm.

*Plant width* (*spread*).—About 34 cm.

*Lateral branches*.—Length: About 14.2 cm. Diameter: About 1 mm. Internode length: About 8 mm. Strength: Moderately strong. Aspect: Upright to outward. Texture: Smooth, glabrous. Color: Close to 138A.

Foliage description:

*Arrangement*.—Alternate, simple; sessile.

*Length*.—About 1.7 cm.

*Width*.—About 7 mm.

*Shape*.—Spatulate.

*Apex*.—Acute to somewhat obtuse.

*Base*.—Cuneate.

*Margin*.—Lobed.

*Texture, upper and lower surfaces*.—Pubescent.

*Venation pattern*.—Pinnate, reticulate.

*Color*.—Developing leaves, upper and lower surfaces: Close to 137C. Fully expanded leaves, upper surface: Close to 137A; venation, close to 137A. Fully expanded leaves, lower surface: Close to 138C; venation, close to 138C.

Inflorescence description:

*Appearance and habit*.—Single composite inflorescence form with ray and disc florets arranged acropetally on a capitulum; inflorescences borne above the foliar plane; uniform and freely flowering habit with about 45 open inflorescences per plant at a time; inflorescences face upright.

*Fragrance*.—None detected.

*Flowering season*.—Plants flower from spring through autumn in Japan; flowering continuous during this period; early flowering habit, plants begin flowering about 50 days after planting.

*Inflorescence longevity*.—Inflorescences last about two to three weeks on the plant; inflorescences persistent.

*Inflorescence bud*.—Height: About 4.4 mm. Diameter: About 3.9 mm. Shape: Ovoid. Color: Close to 6D.

*Inflorescence size*.—Diameter: About 1.8 cm. Height: About 6 mm. Diameter of disc: About 6.3 mm.

*Ray florets*.—Quantity/arrangement: About 32 in one or two whorls. Length: About 5.7 mm. Width: About 1.4 mm. Shape: Lanceolate. Apex: Rounded. Base: Obtuse. Margin: Entire. Texture, upper and lower surfaces: Smooth, glabrous. Color: When opening, upper surface: Close to 7A. When opening, lower surface: Close to 8A. Fully opened, upper surface: Close to 3C. Fully opened, lower surface: Close to 4D.

*Disc florets*.—Quantity/arrangement: About 50 massed at center of receptacle. Shape: Tubular, elongated; five-lobed. Apex: Acute. Length: About 4.1 mm. Width: About 1.1 mm. Texture: Smooth, glabrous. Color, immature: Close to 14A. Color, mature: Close to 6D.

*Involucral bracts*.—Quantity/arrangement: About twelve; bracts imbricate. Length: About 3.2 mm. Width: About 1.5 mm. Shape: Ovate. Apex: Acute. Base: Rounded. Margin: Entire, ciliate. Texture, upper and lower surfaces: Smooth, glabrous. Color, upper and lower surfaces: Close to 138A.

*Peduncles*.—Length: About 5.8 cm. Diameter: About 0.5 mm. Strength: Moderately strong. Texture: Pubescent. Color: Close to 143C.

*Reproductive organs*.—Androecium: Present on disc florets only. Stamen length: About 2.5 mm. Anther length: Less than 1 mm. Anther shape: Lanceolate. Anther color: Close to 7B. Pollen amount: Moderate. Pollen color: Close to 7B. Gynoecium: Present on ray and disc florets. Pistil length: About 2.4 mm. Style color: Close to 7A. Stigma shape: Bi-lobed. Stigma color: Close to 2B. Ovary color: Close to 145B.

*Seeds/fruits*.—Seed and fruit development has not been observed on plants of the new *Brachyscome*.

Disease/pest resistance: Plants of the new *Brachyscome* have not been observed to be resistant to pathogens and pests common to *Brachyscomes.*

Garden performance: Plants of the new *Brachyscome* have been observed to have good garden performance and tolerate rain, wind and temperatures ranging from about 0° C. to about 40° C.

It is claimed:

1. A new and distinct *Brachyscome* plant named 'Bonbra7115' as illustrated and described.

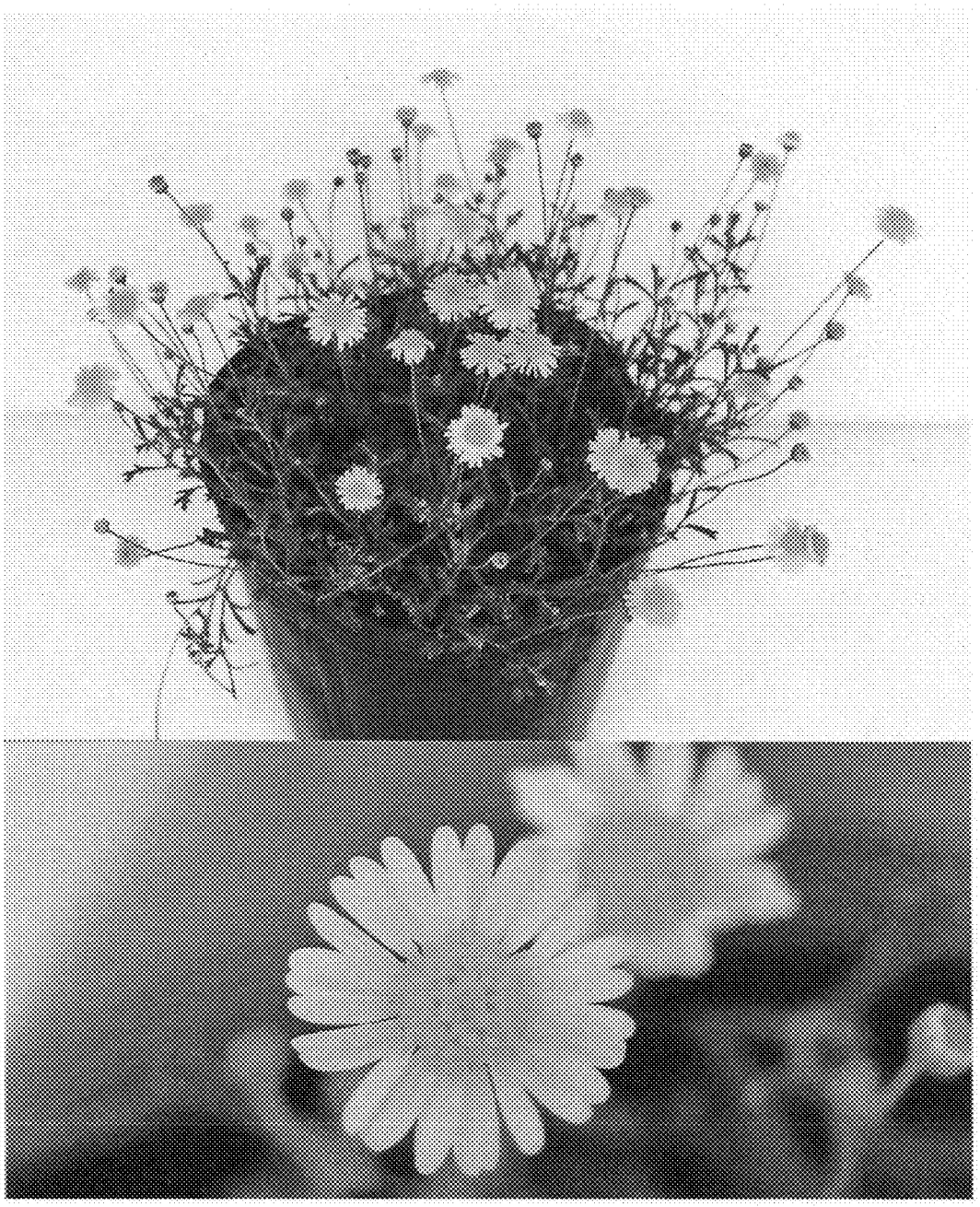

* * * * *